United States Patent
Fryshman

(10) Patent No.: US 12,226,947 B1
(45) Date of Patent: Feb. 18, 2025

(54) SYSTEM FOR FORMING CUSTOM ORTHOTICS

(71) Applicant: Bernard Fryshman, Flushing, NY (US)

(72) Inventor: Bernard Fryshman, Flushing, NY (US)

( * ) Notice: Subject to any disclaimer, the term of this patent is extended or adjusted under 35 U.S.C. 154(b) by 0 days.

(21) Appl. No.: 18/748,386

(22) Filed: Jun. 20, 2024

(51) Int. Cl.
  *B29C 51/00* (2006.01)
  *A61B 5/107* (2006.01)
  *A61F 5/01* (2006.01)
  *B29C 51/18* (2006.01)
  *B29C 51/42* (2006.01)
  *B29C 51/46* (2006.01)
  *B29L 31/00* (2006.01)

(52) U.S. Cl.
  CPC .......... *B29C 51/008* (2013.01); *A61B 5/1078* (2013.01); *A61F 5/01* (2013.01); *B29C 51/18* (2013.01); *B29C 51/421* (2013.01); *B29C 51/46* (2013.01); *B29L 2031/753* (2013.01)

(58) Field of Classification Search
  CPC ...... B29C 51/008; B29D 35/12; B29D 35/128
  See application file for complete search history.

(56) References Cited

U.S. PATENT DOCUMENTS 4,470,782 A * 9/1984 Zimmerman, Jr. ...... A43B 7/28
  264/223

FOREIGN PATENT DOCUMENTS

| DE | 102014010173 | * | 1/2015 |
| FR | 2913210 | * | 9/2008 |
| JP | 4416212 | * | 2/2010 |
| KR | 101258581 | * | 5/2013 |

* cited by examiner

Primary Examiner — Edmund H Lee
(74) Attorney, Agent, or Firm — Bell & Manning, LLC

(57) ABSTRACT

A system for making custom orthotic devices includes a housing, and the housing includes an opening sized to receive a body part. The system also includes a plastic sheet mounted to the housing such that the plastic sheet is in a position to receive pressure from the body part. The system also includes a ferrous material positioned within the housing. The system further includes an electromagnetic source that generates electromagnetic radiation to heat the ferrous material such that, in conjunction with the received pressure, the plastic sheet molds into an orthotic device for the body part.

14 Claims, 6 Drawing Sheets

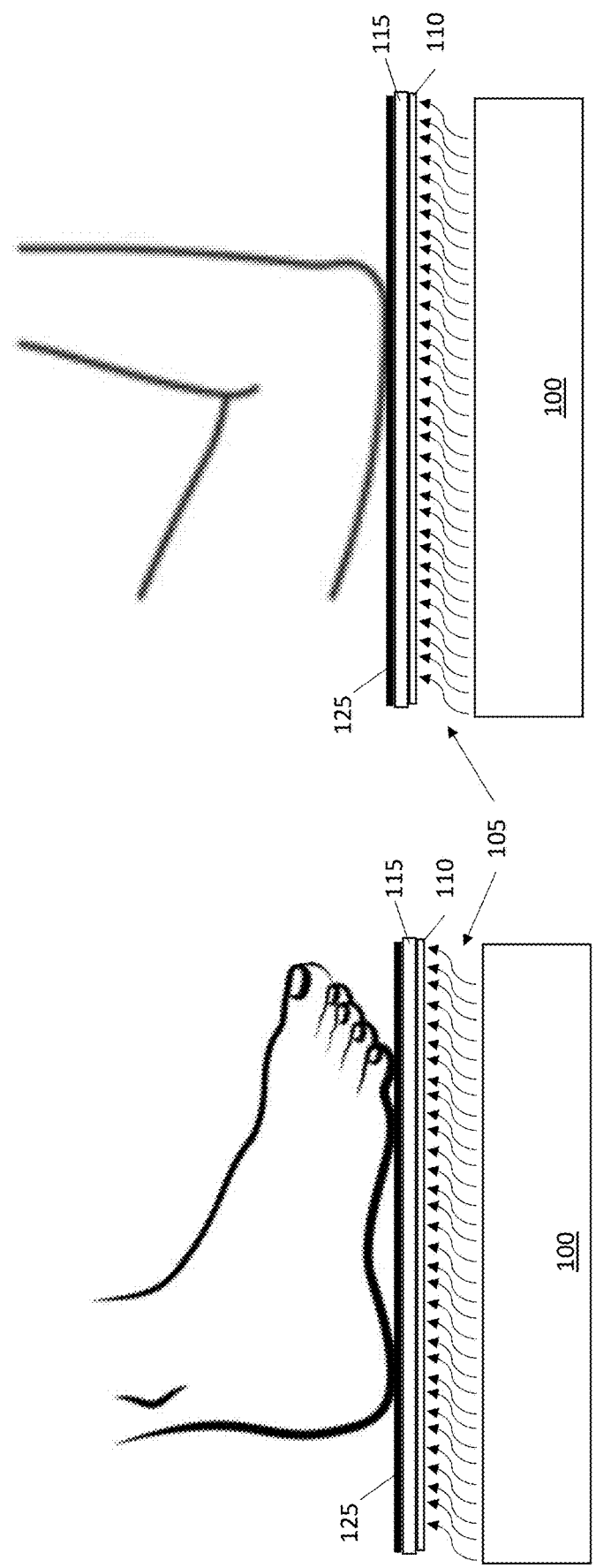

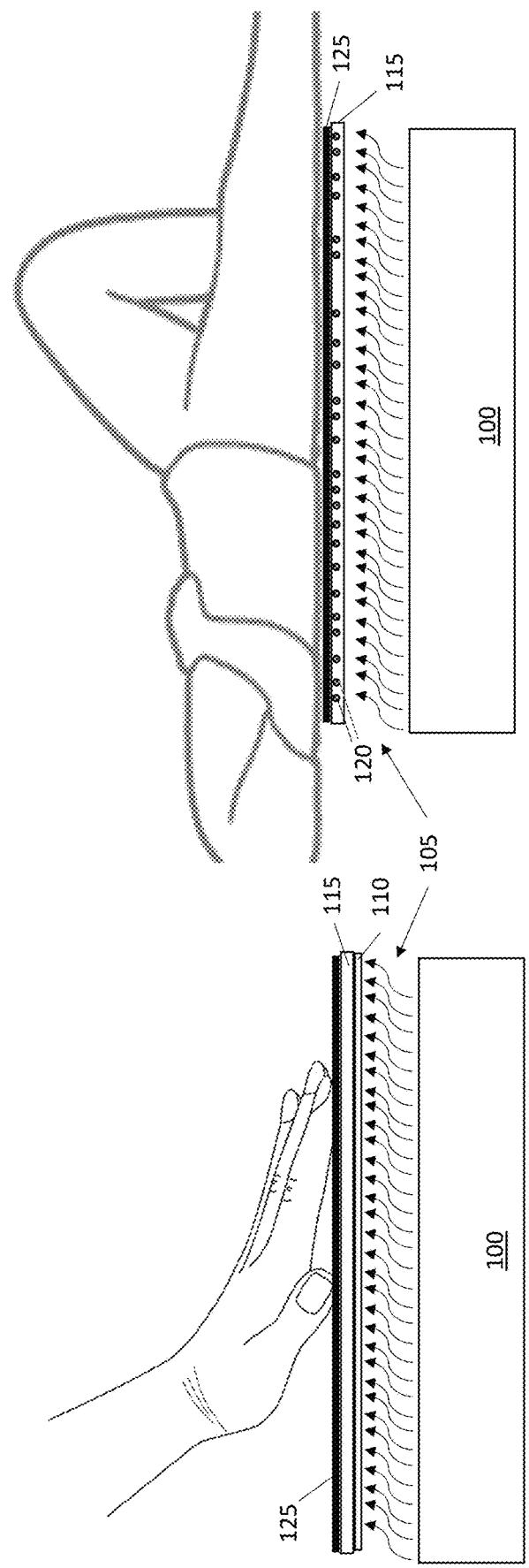

SYSTEM FOR FORMING CUSTOM ORTHOTICS

BACKGROUND

Orthotic devices, or orthoses, refer to braces, calipers, supports, etc. that are used/worn by individuals with various muscular or skeletal issues. When formed and worn properly, orthotic devices are able to influence the structural and/or functional characteristics of the neuromuscular and skeletal systems of the user. Depending on the needs of the user, orthoses can be fabricated to help with the lower extremities, the upper extremities, the trunk, or the head. Given the different sizes and shapes of different individuals, many orthoses have to be custom designed to fit a given patient. This customization process requires precision, and can be time consuming and costly.

SUMMARY

An illustrative system for making custom orthotic devices includes a housing, and the housing includes an opening sized to receive a body part. The system also includes a plastic sheet mounted to the housing such that the plastic sheet is in a position to receive pressure from the body part. The system also includes a ferrous material positioned adjacent to or within the housing. The system further includes an electromagnetic source that generates electromagnetic radiation to heat the ferrous material such that, in conjunction with the received pressure, the plastic sheet molds into an orthotic device for the body part.

In an illustrative embodiment, the system also includes a heat shield mounted between the plastic sheet and the body part. In another embodiment, a temperature sensor is mounted to the heat shield. The system can also include a controller in communication with the temperature sensor, where the controller is configured to receive a sensed temperature from the temperature sensor, compare the sensed temperature to a temperature threshold, and responsive to a determination that the sensed temperature exceeds the temperature threshold, lower a temperature of the heat shield. In one embodiment, the controller activates a motor to move the electromagnetic source away from the plastic sheet to lower the temperature. In another embodiment, the controller activates a motor to move the plastic sheet away from the electromagnetic source to lower the temperature. In another embodiment, the controller turns off the electromagnetic source to lower the temperature. In another embodiment, the controller pulses the electromagnetic source to lower the temperature. In one embodiment, one or more temperature sensors can be mounted on or proximate to the plastic sheet. The one or more sensors can be used to monitor a temperature of the plastic sheet to ensure that the temperature satisfies a predetermined temperature threshold (i.e., the temperature that enables molding of the plastic sheet).

In one embodiment, the system includes a distance sensor mounted within the housing. In another embodiment, the system also includes a controller in communication with the distance sensor, where the controller is configured to receive a sensed distance from the distance sensor, where the sensed distance is between the plastic sheet and the electromagnetic source. The controller also compares the sensed distance to a desired distance between the plastic sheet and the electromagnetic source. Responsive to a determination that the sensed distance differs from the desired distance, the controller moves the electromagnetic source or the plastic sheet to achieve the desired distance.

In one embodiment, the ferrous material comprises ferrous elements embedded within the plastic sheet. In another embodiment, the ferrous elements are positioned between a top surface of the plastic sheet and a center line of the plastic sheet. In another embodiment, the ferrous material is a ferrous metal sheet. In another embodiment, the ferrous metal sheet is mounted in the housing such that a height of the ferrous metal sheet within the housing is adjustable. The ferrous metal sheet can be positioned below the plastic sheet in one embodiment.

An illustrative method for making custom orthotic devices includes mounting a plastic sheet to a housing. The method also includes receiving, by the plastic sheet, pressure from a body part of a patient. The method further includes directing electromagnetic radiation to a ferrous material mounted within the housing, wherein the electromagnetic radiation heats the ferrous material, which heats the plastic sheet such that the plastic sheets forms into an orthotic device that fits the body part.

The method can also include mounting a heat shield to the plastic sheet such that the heat shield is positioned between the plastic sheet and the body part. In one embodiment, a temperature sensor is mounted to the heat shield, and the method further includes receiving, by a controller, a sensed temperature from the temperature sensor, comparing the sensed temperature to a temperature threshold, and responsive to a determination that the sensed temperature exceeds the temperature threshold, lowering a temperature of the heat shield. In one embodiment, the method includes activating, by the controller, a motor to move the plastic sheet away from the electromagnetic source to lower the temperature.

In one embodiment, the ferrous material comprises ferrous elements embedded within the plastic sheet, such that the ferrous elements are positioned between a top surface of the plastic sheet and a center line of the plastic sheet. In another embodiment, the ferrous material comprises a ferrous metal sheet, and the method further includes adjusting, by a controller, a height of the ferrous metal sheet within the housing based at least in part on a sensed distance between the plastic sheet and the ferrous metal sheet.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIG. 1A depicts formation of an orthotic device for a foot in accordance with an illustrative embodiment.

FIG. 1B depicts formation of an orthotic device for an elbow in accordance with an illustrative embodiment.

FIG. 1C depicts formation of an orthotic device for a hand in accordance with an illustrative embodiment.

FIG. 1D depicts formation of an orthotic device of a lower back in accordance with an illustrative embodiment.

Figure 2:
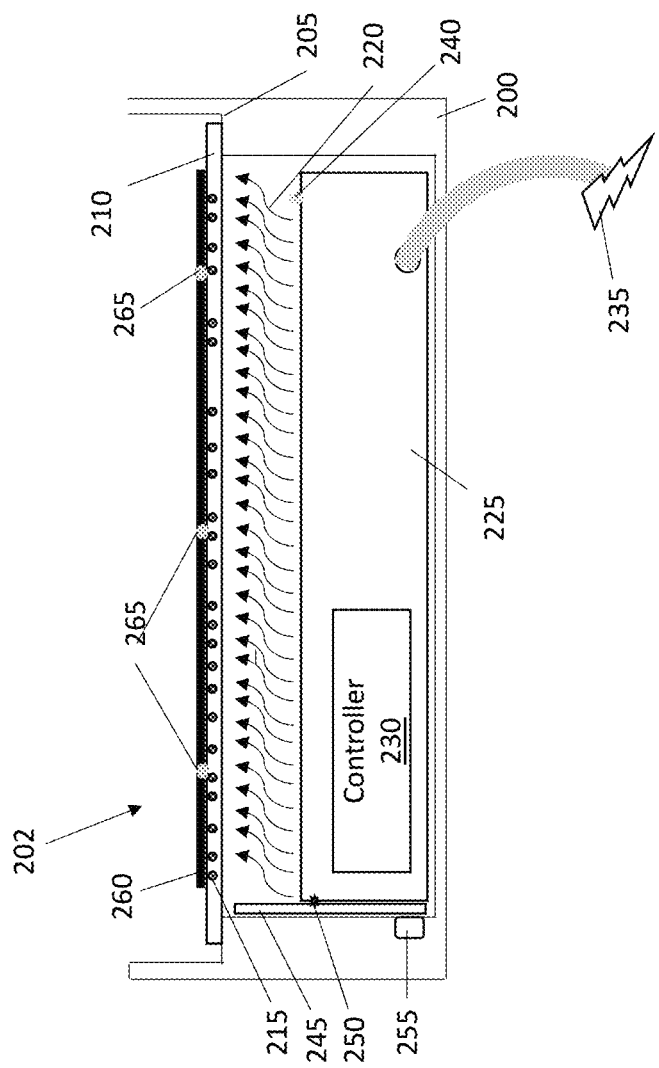
FIG. 2 depicts a system for forming orthotic devices in accordance with an illustrative embodiment.

It is noted that the above-referenced figures are representational, and that they are not intended to be limiting with respect to the form and/or shape of the various embodiments.

DETAILED DESCRIPTION

For many individuals, custom orthotic devices are necessary to lessen or eliminate pain, such as foot pain, knee pain, back pain, neck pain, etc. Traditionally, preparing custom orthotic devices involves casting a mold of a body part, preparing an orthotic shell around the mold, and adding material to improve comfort and fit. The process is exacting and expensive, and increasing numbers of an aging population cannot afford such products, resulting in increased suffering and pain. Additionally, it is often the case that an individual's needs change over time, and that a previously effective orthotic device may no longer work for the individual. As a result, under traditional practices, an entirely new orthotic device is formed to accommodate the individual's new needs. This process is time consuming and results in significant additional cost to the user, since an entirely new orthotic device has been created.

Described herein are methods and systems that utilize induction heating to perform various functions, including forming custom orthotic devices. Induction refers to a heating process in which ferrous material is exposed to electromagnetic radiation, which in turn causes the ferrous material to increase in temperature. The electromagnetic radiation can originate from an electromagnetic generator, rotating magnets, or any other source. In an illustrative embodiment, the electromagnetic radiation emitted from the generator is focused on a region of interest that is to be heated to improve efficiency and to help prevent stray radiation.

More specifically, described herein is an inexpensive, efficient, and quick way to create custom orthotic devices using induction as a safe, local source of heat to prepare the plastic for shaping. Additionally, the user's body (i.e., the region or limb that is being fitted for the orthotic device) can apply pressure to the plastic during the shaping, to ensure that the orthotic device perfectly matches the user's body. Use of the user's body to apply pressure eliminates the need to form a separate mold, which saves money and significantly decreases the amount of time that it takes to form the orthotic device.

As discussed, the orthotic device can be made of a plastic, and inductive heating of ferrous material is used to mold the plastic to the user such that a perfect fit can be achieved. Additionally, if the needs of the user change over time, the custom orthotic device can easily be remolded down the road to again provide a perfect fit for the user. The plastic used can be acrylic, polycarbonate, polyethylene, polypropylene, and/or any other type of plastic that can be thermoformed. The ferrous material can be positioned above the plastic that is to be formed into the orthotic device, below the plastic, and/or impregnated into the plastic, depending on the embodiment.

In an illustrative embodiment, the plastic which forms the orthotic device may be heated to a high temperature to enable thermoforming in accordance with the pressure applied by the body part(s) of the user. To protect the user from burns, a heat shield can be placed in between the user's skin and the plastic sheet that is used to form the orthotic device. The heat shield can be formed from Kevlar, Nomex, or any other heat resistant material(s). In an illustrative embodiment, the heat shield is flexible such that the heat shield takes on the shape of the user's body part as the orthotic device is being thermoformed.

FIG. 1 depicts a system for making orthotic devices, and various body parts for which the orthotic devices can be made. Specifically, FIG. 1A depicts formation of an orthotic device for a foot in accordance with an illustrative embodiment. FIG. 1B depicts formation of an orthotic device for an elbow in accordance with an illustrative embodiment. FIG. 1C depicts formation of an orthotic device for a hand in accordance with an illustrative embodiment. FIG. 1D depicts formation of an orthotic device of a lower back in accordance with an illustrative embodiment. While various body parts are shown, it is to be understood that the system is not limited to making orthotic devices for those body parts. In alternative embodiments, the system can be used to form any orthotic device for any body part, including the knees, neck, head, thigh, calf, upper arm, shoulder, etc.

As shown, an electromagnetic source 100 generates electromagnetic radiation 105. In one embodiment, the electromagnetic radiation 105 interacts with a thin sheet of ferrous material 110, which results in inductive heating of the sheet of ferrous material 110. The heated sheet of ferrous material 110 in turn heats a plastic sheet 115 that is positioned adjacent to the sheet of ferrous material 110. Upon being heated, pressure from a body part (e.g., foot, hand, back, etc.) causes the plastic sheet 115 to form around the body part, resulting in formation the orthotic device. Upon removal of the electromagnetic radiation, the plastic sheet 115 cools and hardens, resulting in a sturdy orthotic device. In an illustrative embodiment, the sheet of ferrous material 110 is thin and flexible such that the sheet of ferrous material changes shape in accordance with plastic sheet 115 as the orthotic device is being formed from the inductive heating and body part pressure. In the embodiments shown, the sheet of ferrous material 110 is positioned below the plastic sheet 115. In an alternative embodiment, the sheet of ferrous material 110 can be positioned on top of the plastic sheet 115.

In an alternative embodiment, the sheet of ferrous material 110 may be rigid such that the sheet of ferrous material 110 does not take on the shape of the orthotic device as the plastic sheet 115 is being molded in response to the inductive heat and pressure from the patient's body part that is to be placed in the orthotic device. In such an embodiment, the sheet of ferrous material 110 can be movable, and can be positioned a distance below the plastic sheet 115. The distance at which the sheet of ferrous material 110 is positioned below the plastic sheet 115 can be based on the size and/or type of the orthotic device being formed. For example, if the orthotic device is expected (or estimated) to be 4 inches deep, the sheet of ferrous material 110 can be positioned at least 4 inches below the plastic sheet 115 to ensure that there is sufficient space for the orthotic device to be formed from the plastic sheet 115. The distance between the sheets can also be greater than the estimated depth of the orthotic device (e.g., 0.25-3 inches greater) to ensure that the plastic sheet 115 does not contact the sheet of ferrous material 110.

In another alternative embodiment, instead of a sheet of ferrous material, ferrous elements 120 can be incorporated (i.e., embedded) into the plastic sheet 115, as shown in FIG. 1D. Upon receiving radiation from the electromagnetic source 100, the ferrous elements 120 are heated inductively, which in turn heats the plastic sheet 115 into which the ferrous elements 120 are embedded. The ferrous elements 120 are particles of ferrous material that can vary in size in one embodiment. Alternatively, the ferrous elements 120 can all be the same size. In an illustrative embodiment, the ferrous elements 120 are evenly distributed throughout the plastic sheet 115.

As shown in FIGS. 1A-1D, a heat shield 125 is positioned between the body part of the patient/user and the plastic sheet. The heat shield 125 is flexible such that the heat shield 125 changes shape in accordance with the plastic sheet 11 as the orthotic device is being formed from the inducting heating of the sheet of ferrous material or the ferrous elements. The heat shield 125 can be made from Kevlar, Nomex, or any other heat resistant material that is flexible enough to change shape along with the plastic sheet as the orthotic device is being formed.

FIG. 2 depicts a system for forming orthotic devices in accordance with an illustrative embodiment. The system includes a housing 200 that houses the various system components. In the embodiment shown, the housing 200 includes an upper opening 202 that is sized to receive a body part such that pressure can be applied as discussed above. In another embodiment, an upper surface of the housing 200 can be flat such that a patient can lay on/over the system and apply pressure via the body trunk. In the embodiment of FIG. 2, the housing also includes a shelf 205 that supports edges of a plastic sheet 210 that is to be formed into an orthotic device. The shelf 205 allows the edges of the plastic sheet 210 to remain stationary while a central portion of the plastic sheet 210 is molded to form the orthotic device. In the embodiment shown, the plastic sheet 210 includes ferrous elements 215 embedded therein. The ferrous elements 215 receive radiation 220 from an electromagnetic source 225 that is positioned within the housing 200.

Also positioned within the housing 200 is a controller 230 that is used to control delivery of the electromagnetic radiation to the plastic sheet 210. The controller 230 can include a processor, memory, user interface, input/output system, transceiver, and/or any other computing components. The controller 230 and the electromagnetic source 225 are connected to a power source 235, which can be a wall outlet, a battery, a capacitor, etc. The controller 230 is described in more detail below.

In one embodiment, the controller 230 can control a position (i.e., height) of the electromagnetic source 225 based on an estimated depth of the orthotic device that is to be formed. For example, if the estimated depth of the orthotic device is 3 inches, the electromagnetic source 225 may be positioned at least 3 inches away from the plastic sheet 210 to help ensure that the electromagnetic source 225 does not come into contact with the plastic sheet 210. In another embodiment, a distance sensor 240 is used to determine a distance in real time between the electromagnetic source 225 and the plastic sheet 210. In the embodiment shown, the distance sensor is mounted on the electromagnetic source 225. Alternatively, the distance sensor 240 may be mounted to the plastic sheet 210, the housing 200, or the controller 230. Any type of distance measuring sensor may be used. The controller 230 can then dynamically control movement of the electromagnetic source 225 (and/or the plastic sheet 210) to ensure that the electromagnetic source 225 remains a desired distance away from the plastic sheet 210 as the plastic sheet 210 deforms during formation of the orthotic device. The desired distance can be 0.25 inches, 0.5 inches, 1 inch, etc.

In one embodiment, the electromagnetic source 225 is mounted to a track 245 via a gear 250, and a motor 255 can be used to control vertical movement of the electromagnetic source. In another embodiment, a similar setup (i.e., track, gear, and motor) can be used to control horizontal movement of the electromagnetic source 225 within the housing 200. In an alternative embodiment, movement of the electromagnetic source can be performed manually, or using a different automated technique. In another alternative embodiment, the plastic sheet 210 may be mounted such that it is movable relative to the electromagnetic source 225. In another embodiment, both the plastic sheet 210 and the electromagnetic source 225 can be movable during formation of the orthotic device.

The system of FIG. 2 also includes a heat shield 260 that is positioned between the patient's body part (not shown) and the plastic sheet 210 that is to be heated and formed into the orthotic device in response to induction heating and pressure from the patient's body part. The heat shield 260 includes a plurality of temperature sensors 265 that are used by the controller to monitor the temperature of the heat shield 260. This monitoring helps ensure that the patient is not burned during the orthotic device formation process. For example, a temperature threshold can be set as a maximum acceptable temperature of an exterior surface of the heat shield so that the user is not burned. The temperature threshold can be set to any desired value, such as 110° Fahrenheit (F), 120° F., 125° F., 130° F., etc. Any type of temperature sensor may be used, and the temperature sensors can communicate with the controller 230 through a wired or wireless connection, depending on the embodiment. FIG. 2 depicts three temperatures sensors 265 on the heat shield 260. In alternative embodiments, fewer (e.g., 1 or 2) or additional (e.g., 4, 6, 10, etc.) temperature sensors may be used.

In an illustrative embodiment, if the temperature threshold for the heat shield 260 is exceeded (as determined by temperature sensor readings received by the controller 230), the controller 230 can operate the motor 255 to move the electromagnetic source 225 further from the plastic sheet 210 to lower the temperature. In another embodiment, in response to the threshold temperature being exceeded, the controller 230 can operate a motor to move the plastic sheet 210 further from the electromagnetic source 225. In another embodiment, in response to the threshold temperature being exceeded, the controller 230 can reduce an intensity of the electromagnetic radiation 220 that is emitted from the electromagnetic source 225. In another embodiment, in response to the threshold temperature being exceeded, the controller 230 can turn off the electromagnetic source 225 for a period of time until the detected temperature is within the temperature threshold. The controller 230 can also pulse the electromagnetic source 225 on and off at a set interval (e.g., 1 second on, 1 second off; 2 seconds on, 2 seconds off, etc.) until the temperature detected at the temperature sensors 265 is within the temperature threshold. In another embodiment, one or more temperature sensors can be mounted on or proximate to the plastic sheet. The one or more sensors can be used to monitor a temperature of the plastic sheet to ensure that the temperature satisfies a predetermined temperature threshold (i.e., the temperature that enables molding of the plastic sheet).

Figure 3:
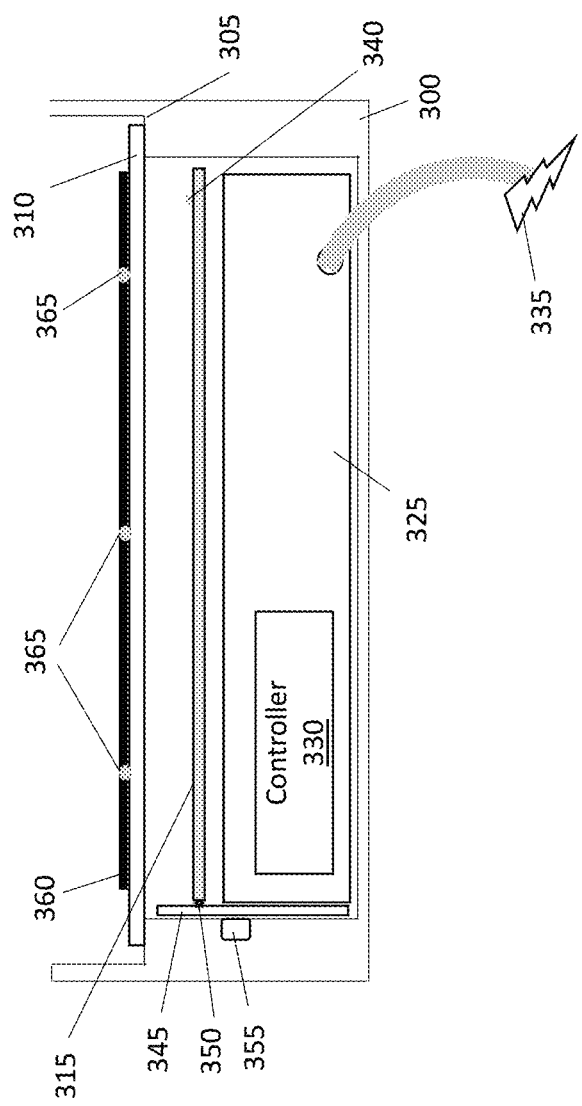
FIG. 3 depicts a system for forming orthotic devices in accordance with another illustrative embodiment.

FIG. 3 depicts a system for forming orthotic devices in accordance with another illustrative embodiment. The system includes a housing 300 that houses the various system components. Similar to the embodiment of FIG. 2, the housing 300 includes a shelf 305 that supports edges of a plastic sheet 310 that is to be formed into an orthotic device. The shelf 305 allows the edges of the plastic sheet 310 to remain stationary while a central portion of the plastic sheet 310 is molded to form the orthotic device. In the embodiment shown, the plastic sheet 310 does not include ferrous elements embedded therein. Rather, the system includes a ferrous metal sheet 315 that receives radiation from an electromagnetic source 325 that is positioned within the housing 300. The electromagnetic radiation causes the ferrous metal sheet 315 to heat up, which in turn heats the plastic sheet 310 so that it is formed into an orthotic device for a body part that is placing pressure onto the plastic sheet 310. It is noted that a depiction of the electromagnetic radiation emitted from the electromagnetic source 325 is not included in FIG. 3 for clarity.

Also positioned within the housing 300 is a controller 330 that is used to control delivery of the electromagnetic radiation to the plastic sheet 310. The controller 330 can include a processor, memory, user interface, input/output system, transceiver, and/or any other computing components. The controller 330 and the electromagnetic source 325 are connected to a power source 335, which can be a wall outlet, a battery, a capacitor, etc. The controller 330 is described in more detail below.

In one embodiment, the controller 330 can control a position (i.e., height) of the ferrous metal sheet 315 based on an estimated depth of the orthotic device that is to be formed. For example, if the estimated depth of the orthotic device is 3 inches, the ferrous metal sheet 315 may be positioned at least 3 inches away from the plastic sheet 310 to help ensure that the ferrous metal sheet 315 does not come into contact with the plastic sheet 310. In alternative embodiments, the plastic sheet 310 can come into contact with the ferrous metal sheet 315. In another embodiment, a distance sensor 340 is used to determine a distance in real time between the ferrous metal sheet 315 and the plastic sheet 310. In the embodiment shown, the distance sensor 340 is mounted on the ferrous metal sheet 315. Alternatively, the distance sensor 340 may be mounted to the plastic sheet 310, the housing 300, or the controller 330. Any type of distance measuring sensor may be used. The controller 330 can then dynamically control movement of the ferrous metal sheet 315 (and/or the plastic sheet 210) to ensure that the ferrous metal sheet 315 remains a desired distance away from the plastic sheet 310 as the plastic sheet 310 deforms during formation of the orthotic device. The desired distance can be 0.25 inches, 0.5 inches, 1 inch, etc.

In one embodiment, the ferrous metal sheet 315 is mounted to a track 345 via a gear 350, and a motor 355 can be used to control vertical movement of the ferrous metal sheet 315. In another embodiment, a similar setup (i.e., track, gear, and motor) can be used to control horizontal movement of the ferrous metal sheet 315 within the housing 300. In an alternative embodiment, movement of the ferrous metal sheet 315 can be performed manually, or using a different automated technique. In another alternative embodiment, the plastic sheet 310 may be mounted such that it is movable relative to the ferrous metal sheet 315. In another embodiment, both the plastic sheet 310 and the ferrous metal sheet 315 can be movable during formation of the orthotic device.

The system of FIG. 3 also includes a heat shield 360 that is positioned between the patient's body part (not shown) and the plastic sheet 310 that is to be heated and formed into the orthotic device in response to induction heating and pressure from the patient's body part. The heat shield 360 includes a plurality of temperature sensors 365 that are used by the controller to monitor the temperature of the heat shield 360. This monitoring helps ensure that the patient is not burned during the orthotic device formation process. For example, a temperature threshold can be set as a maximum acceptable temperature of an exterior surface of the heat shield so that the user is not burned. The temperature threshold can be set to any desired value, such as 110° Fahrenheit (F), 120° F., 125° F., 130° F., etc. Any type of temperature sensor may be used, and the temperature sensors can communicate with the controller 330 through a wired or wireless connection, depending on the embodiment. FIG. 3 depicts three temperatures sensors 365 on the heat shield 360. In alternative embodiments, fewer (e.g., 1 or 2) or additional (e.g., 4, 6, 10, etc.) temperature sensors may be used.

In an illustrative embodiment, if the temperature threshold for the heat shield 360 is exceeded (as determined by temperature sensor readings received by the controller 330), the controller 330 can operate the motor 355 to move the ferrous metal sheet 315 further from the plastic sheet 310 to lower the temperature. In another embodiment, in response to the threshold temperature being exceeded, the controller 330 can operate a motor to move the plastic sheet 310 further from the ferrous metal sheet 315. In another embodiment, in response to the threshold temperature being exceeded, the controller 330 can reduce an intensity of the electromagnetic radiation that is emitted from the electromagnetic source 325, which lowers the temperature of the ferrous metal plate 315, thereby lowering the temperature detected by the temperatures sensors 365. In another embodiment, in response to the threshold temperature being exceeded, the controller 330 can turn off the electromagnetic source 325 for a period of time until the detected temperature is within the temperature threshold. The controller 330 can also pulse the electromagnetic source 325 on and off at a set interval (e.g., 1 second on, 1 second off; 2 seconds on, 2 seconds off, etc.) until the temperature detected at the temperature sensors 365 is within the temperature threshold.

Figure 4:
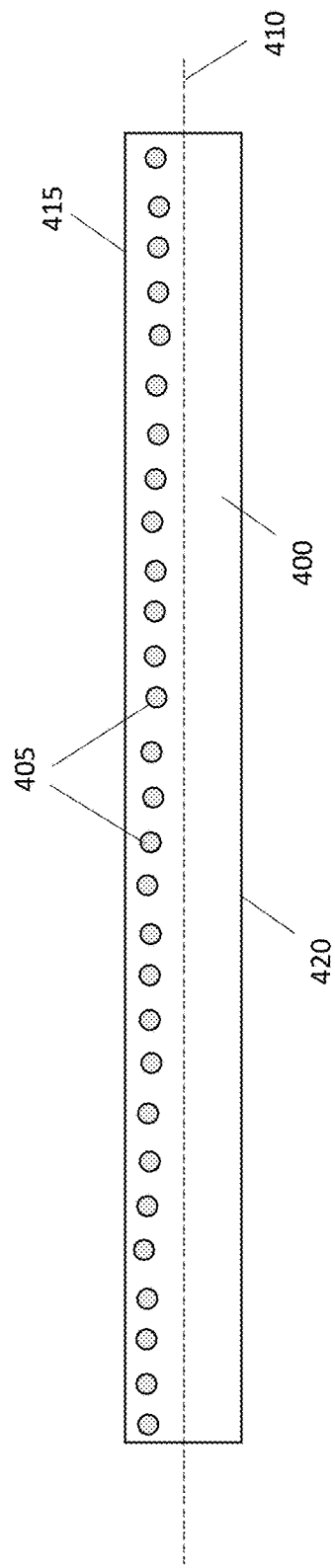
FIG. 4 depicts a plastic sheet with embedded ferrous elements in accordance with an illustrative embodiment.

FIG. 4 depicts a plastic sheet 400 with embedded ferrous elements 405 in accordance with an illustrative embodiment. In the embodiment shown, a center line 410 divides a top portion of the plastic sheet 400 (having a top surface 415) from a bottom portion of the plastic sheet (having a bottom surface 420). As shown, the embedded ferrous elements 405 are positioned between the center line 410 of the plastic sheet 400 and the top surface 415 of the plastic sheet. As such, the embedded ferrous elements 405 are positioned close to the source of pressure (i.e., the body part) to help facilitate molding of the orthotic device from the plastic sheet 400. In an alternative embodiments, the embedded ferrous elements 405 can be positioned on the center line 410, between the center line 410 and the bottom surface 420 of the plastic sheet 400 (i.e., to maximize distance between the ferrous elements and the body part), or randomly distributed throughout the plastic sheet 400.

Figure 5:
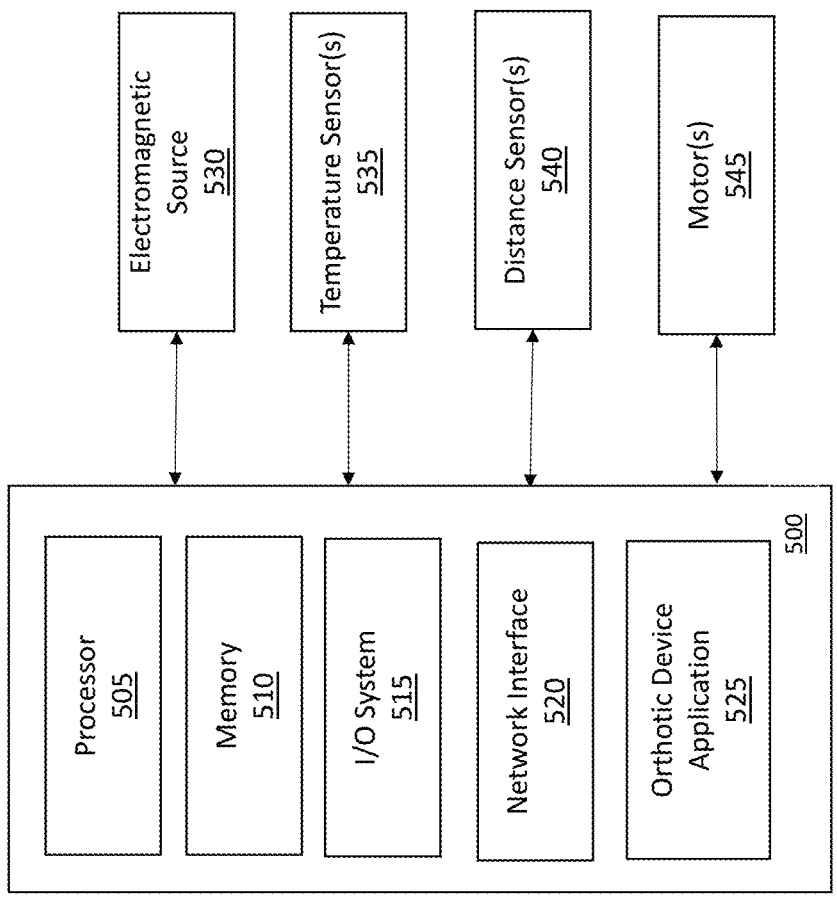
FIG. 5 is a block diagram of a computing device that operates as a system controller in accordance with an illustrative embodiment.

In an illustrative embodiment, the controller described herein may be implemented at least in part as a computing device that uses computer-readable instructions stored on a computer-readable medium, such as a computer memory or storage device. Upon execution of the computer-readable instructions by a processor, the computer-readable instructions may cause the computing device to perform the operations described herein. As an example, FIG. 5 is a block diagram of a computing device that operates as a system controller 500 in accordance with an illustrative embodiment. The system controller 500 includes a processor 505, a memory 510, an input/output (I/O) system 515, a network interface 520, and an orthotic device application 525. In alternative embodiments, the controller 500 may include fewer, additional, and/or different components. The components of the controller 500 communicate with one another via circuit board traces, one or more buses, or any other interconnect system.

As shown, the controller 500 is in communication with an electromagnetic source 530 (which can be any of the electromagnetic sources described herein), one or more temperature sensors 535 (which can be any of the temperature sensors described herein), one or more distance sensors 540 (which can be any of the distance sensors described herein), and one or more motors 545 (which can be any of the motors described herein). The controller 500 is used to interact with and control these components as discussed above. The controller 500 can also communication with a network, such as the Internet, in some embodiments and/or other devices such as smartphones, laptops, servers, databases, etc.

The processor 505 of the controller 500 can be in electrical communication with and used to perform any of the operations described herein, such as gathering sensed data, processing the gathered data, controlling the motors to control a position of components within the system, controlling the electromagnetic source 530 to maintain a desired temperature, etc. The processor 505 can be any type of computer processor known in the art, and can include a plurality of processors and/or a plurality of processing cores. The processor 505 can include a controller, a microcontroller, an audio processor, a graphics processing unit, a hardware accelerator, a digital signal processor, etc. Additionally, the processor 505 may be implemented as a complex instruction set computer processor, a reduced instruction set computer processor, an x86 instruction set computer processor, etc.

The memory 510 is used to store programs, algorithms, network and communications data, peripheral component data, the orthotic device application 525, and other operating instructions. The memory 510 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 515, or user interface, is the framework which enables users (and peripheral devices) to interact with the controller 500. In alternative embodiments, the I/O system 515 can be on a remote computing device, such as a user device that is used to control the controller 500 remotely. The I/O system 515 can include one or more keys or a keyboard, one or more buttons, a speaker, a microphone, a display, etc. The I/O system 515 allows the user to interact with and control the controller system 500. The I/O system 515 can also include circuitry and a bus structure to interface with and control peripheral computing components such as one or more power sources, etc.

The network interface 520 includes transceiver circuitry (e.g., a receiver and/or a transmitter) that allows the controller 500 to transmit and receive data to/from other devices such as the temperature sensor(s) 535, the distance sensor(s) 540, etc. In one embodiment, the network interface 520 enables communication through a network, which can be one or more communication networks. The network can include a cable network, a fiber network, a cellular network, a wi-fi network, a landline telephone network, a microwave network, a satellite network, etc. The network interface 520 also includes circuitry to allow device-to-device communication such as near field communication (NFC), Bluetooth® communication, etc.

The orthotic device application 525 can include software and algorithms (e.g., in the form of computer-readable instructions) which, upon activation or execution by the processor 505, performs any of the various operations described herein such as activating sensors, recording sensed data, processing the sensed data to determine information plastic sheet temperature, heat shield temperature, distance of a ferrous metal sheet from the plastic sheet, distance of the electromagnetic source from the ferrous metal sheet and/or the plastic sheet, comparison of sensed values to thresholds, controlling of motors to move system components, etc. The orthotic device application 525 can utilize the processor 505 and/or the memory 510 as discussed above.

Thus, described herein are methods and systems for forming/molding orthotic devices. The proposed methods and systems can also be used to form/mold other components such as helmets, hats, baseball bats, industrial equipment, etc. The proposed methods and systems are safer than alternative processes, many of which involve flames and/or extreme heat to induce molding. The proposed methods and systems are also less costly than traditional techniques because the need to separately form a precise mold is eliminated using the current system. The proposed system also saves costs because an orthotic device (or other object) can quickly and easily be remolded (i.e., without having to start from scratch and produce an entirely new device) in the event that the patient's needs change.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system for making custom orthotic devices, the system comprising:
    a housing, wherein the housing includes an opening sized to receive a body part;
    a plastic sheet mounted to the housing such that the plastic sheet is in a position to receive pressure from the body part;
    a ferrous material positioned within the housing; and
    an electromagnetic source that generates electromagnetic radiation to heat the ferrous material such that, in conjunction with the received pressure, the plastic sheet molds into an orthotic device for the body part.

2. The system of claim 1, further comprising a heat shield mounted between the plastic sheet and the body part.

3. The system of claim 2, further comprising a temperature sensor mounted to the heat shield.

4. The system of claim 3, further comprising a controller in communication with the temperature sensor, wherein the controller is configured to:
receive a sensed temperature from the temperature sensor;
compare the sensed temperature to a temperature threshold; and
responsive to a determination that the sensed temperature exceeds the temperature threshold, lower a temperature of the heat shield.

5. The system of claim 4, wherein the controller activates a motor to move the electromagnetic source away from the plastic sheet to lower the temperature.

6. The system of claim 4, wherein the controller activates a motor to move the plastic sheet away from the electromagnetic source to lower the temperature.

7. The system of claim 4, wherein the controller turns off the electromagnetic source to lower the temperature.

8. The system of claim 4, wherein the controller pulses the electromagnetic source to lower the temperature.

9. The system of claim 1, further comprising a distance sensor mounted within the housing.

10. The system of claim 9, further comprising a controller in communication with the distance sensor, wherein the controller is configured to:
receive a sensed distance from the distance sensor, wherein the sensed distance is between the plastic sheet and the electromagnetic source;
compare the sensed distance to a desired distance between the plastic sheet and the electromagnetic source; and
responsive to a determination that the sensed distance differs from the desired distance, move the electromagnetic source or the plastic sheet to achieve the desired distance.

11. The system of claim 1, wherein the ferrous material comprises ferrous elements embedded within the plastic sheet.

12. The system of claim 11, wherein the ferrous elements are positioned between a top surface of the plastic sheet and a center line of the plastic sheet.

13. The system of claim 1, wherein the ferrous material comprises a ferrous metal sheet.

14. The system of claim 13, wherein the ferrous metal sheet is mounted in the housing such that a height of the ferrous metal sheet within the housing is adjustable.

* * * * *